(12) United States Patent
Kim et al.

(10) Patent No.: US 11,663,305 B2
(45) Date of Patent: *May 30, 2023

(54) CONTROLLING INPUT/OUTPUT DEVICES

(71) Applicant: Samsung Electronics Co., Ltd., Gyeonggi-do (KR)

(72) Inventors: Hyun-Soo Kim, Gyeonggi-do (KR); Hyun-Seok Shin, Gyeonggi-do (KR); Jong-Min Choi, Seoul (KR); Cheol-Ho Cheong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,169

(22) Filed: Dec. 28, 2018

(65) Prior Publication Data
US 2019/0138705 A1    May 9, 2019

Related U.S. Application Data

(63) Continuation of application No. 14/536,971, filed on Nov. 10, 2014, now Pat. No. 10,169,559.

(30) Foreign Application Priority Data

Feb. 21, 2014   (KR) .................. 10-2014-0020477

(51) Int. Cl.
*H04N 7/16*     (2011.01)
*G06F 21/32*    (2013.01)
(Continued)

(52) U.S. Cl.
CPC ............ *G06F 21/32* (2013.01); *A61B 5/6844* (2013.01); *A61B 5/6898* (2013.01); *G06F 1/163* (2013.01); *G06F 1/3231* (2013.01); *G06F 1/3287* (2013.01); *G06F 13/102* (2013.01); *H04M 1/72412* (2021.01); *H04M 1/72454* (2021.01); *A61B 5/02405* (2013.01); *A61B 5/02438* (2013.01); *A61B 5/1112* (2013.01);
(Continued)

(58) Field of Classification Search
USPC ............................................ 726/19; 713/186
See application file for complete search history.

(56) References Cited

U.S. PATENT DOCUMENTS 5,774,784 A   6/1998   Ohno
6,307,480 B1  10/2001  Sheldon et al.
(Continued)

FOREIGN PATENT DOCUMENTS

EP   1 983 732 A1   10/2008
KR   0120590 Y1    4/1998
(Continued)

OTHER PUBLICATIONS

Korean Search Report dated Jan. 30, 2020.

*Primary Examiner* — Amare F Tabor
(74) *Attorney, Agent, or Firm* — Cha & Reiter, LLC

(57) ABSTRACT

An electronic device is provided processor configured to: receive a biological signal of a user; detect whether the electronic device is attached to or detached from the user based on at least the biological signal; and control an I/O device operationally connected to the electronic device based on whether the electronic device is attached to or detached from the user.

23 Claims, 5 Drawing Sheets

(51) Int. Cl.
 *G06F 1/16* (2006.01)
 *G06F 1/3231* (2019.01)
 *G06F 1/3287* (2019.01)
 *A61B 5/00* (2006.01)
 *H04M 1/72412* (2021.01)
 *H04M 1/72454* (2021.01)
 *G06F 13/10* (2006.01)
 *A61B 5/024* (2006.01)
 *H04M 1/67* (2006.01)
 *A61B 5/11* (2006.01)
 *A61B 5/318* (2021.01)
 *A61B 5/369* (2021.01)
 *A61B 5/389* (2021.01)

(52) U.S. Cl.
 CPC .............. *A61B 5/318* (2021.01); *A61B 5/369* (2021.01); *A61B 5/389* (2021.01); *A61B 5/4869* (2013.01); *H04M 1/67* (2013.01); *H04M 2250/12* (2013.01); *Y02D 10/00* (2018.01)

(56) References Cited

U.S. PATENT DOCUMENTS

| | | | |
|---|---|---|---|
| 6,527,711 B1 * | 3/2003 | Stivoric | A61B 5/0002 128/898 |
| 6,983,061 B2 | 1/2006 | Ikegami et al. | |
| 7,222,239 B2 | 5/2007 | Smith | |
| 7,404,081 B2 | 7/2008 | Murashita | |
| 7,649,456 B2 | 1/2010 | Wakefield et al. | |
| 7,711,961 B2 | 5/2010 | Fujinuma et al. | |
| 7,712,675 B2 | 5/2010 | Balinsky et al. | |
| 7,809,954 B2 | 10/2010 | Miller et al. | |
| 8,054,160 B2 | 11/2011 | Corrado et al. | |
| 8,289,130 B2 | 10/2012 | Nakajima et al. | |
| 8,344,998 B2 * | 1/2013 | Fitzgerald | G06F 1/3203 345/156 |
| 8,541,745 B2 * | 9/2013 | Dickinson | G04G 21/00 250/340 |
| 8,844,007 B2 | 9/2014 | Vicente et al. | |
| 8,898,564 B2 * | 11/2014 | Grant | G06F 1/3231 715/702 |
| 8,948,145 B2 | 2/2015 | Kalbag | |
| 8,948,745 B2 * | 2/2015 | Moore | H04W 12/12 455/425 |
| 9,086,875 B2 * | 7/2015 | Harrat | G06F 1/3203 |
| 9,186,077 B2 * | 11/2015 | Ma | A61B 5/02438 |
| 9,727,139 B2 * | 8/2017 | Ramsay | A61B 5/0002 |
| 2002/0095587 A1 | 7/2002 | Doyle et al. | |
| 2005/0071647 A1 | 3/2005 | Fujinuma et al. | |
| 2006/0288233 A1 | 12/2006 | Kozlay | |
| 2007/0255961 A1 | 11/2007 | Tracy et al. | |
| 2007/0280515 A1 | 12/2007 | Goto | |
| 2009/0153470 A1 * | 6/2009 | Chen | G06F 1/1624 345/156 |
| 2009/0234614 A1 | 9/2009 | Kahn et al. | |
| 2009/0271644 A1 | 10/2009 | Fiebrich et al. | |
| 2010/0081411 A1 | 4/2010 | Montenero | |
| 2010/0134327 A1 * | 6/2010 | Dinh | G06F 3/014 341/20 |
| 2010/0152620 A1 * | 6/2010 | Ramsay | A61B 5/0002 600/595 |
| 2011/0208984 A1 | 8/2011 | Naware et al. | |
| 2011/0224509 A1 | 9/2011 | Fish et al. | |
| 2012/0221254 A1 | 8/2012 | Kateraas et al. | |
| 2013/0109997 A1 | 5/2013 | Linke et al. | |
| 2013/0119255 A1 | 5/2013 | Dickinson et al. | |
| 2013/0145184 A1 | 6/2013 | Tatsumoto et al. | |
| 2013/0217978 A1 | 8/2013 | Ma | |
| 2014/0032953 A1 | 1/2014 | Wei et al. | |
| 2014/0160035 A1 | 6/2014 | Sauer et al. | |
| 2014/0165185 A1 | 6/2014 | Lange | |
| 2014/0218497 A1 | 8/2014 | Hanna et al. | |
| 2014/0313863 A1 | 10/2014 | Lee et al. | |
| 2015/0020081 A1 | 1/2015 | Cho et al. | |
| 2015/0026647 A1 | 1/2015 | Park et al. | |
| 2015/0033283 A1 | 1/2015 | Mulder | |
| 2015/0065164 A1 | 3/2015 | Hoseinitabatabaei et al. | |
| 2015/0077234 A1 * | 3/2015 | Fullam | G09B 21/003 340/407.1 |
| 2015/0186628 A1 | 7/2015 | Bush et al. | |
| 2016/0220865 A1 * | 8/2016 | Seo | G16H 40/63 |

FOREIGN PATENT DOCUMENTS

| | | |
|---|---|---|
| KR | 10-2005-0021270 A | 3/2005 |
| KR | 10-2007-0058869 A | 6/2007 |
| KR | 10-2012-0135258 A | 12/2012 |
| KR | 10-1725541 B1 | 4/2017 |

\* cited by examiner

CONTROLLING INPUT/OUTPUT DEVICES

CROSS REFERENCE TO RELATED APPLICATIONS

This application is a Continuation of U.S. patent application Ser. No. 14/536,971 filed on Nov. 10, 2014 which claims priority under 35 U.S.C. § 119(a) from Korean patent application Serial No. 10-2014-0020477, which was filed in the Korean Intellectual Property Office on Feb. 21, 2014, the entire disclosure of which is hereby incorporated by reference.

TECHNICAL FIELD

The present disclosure relates to an electronic device and more particularly to controlling I/O devices.

BACKGROUND

As electronic devices (e.g., smart phones) or wearable devices grow to have better performance, they have now more various input/output (I/O) devices. For example, the electronic device may include input devices like a touch panel for receiving touching (or hovering) inputs or microphones for receiving voice inputs and output devices like a display for displaying visual information, a speaker for outputting audio information, or a haptic device for outputting haptic information (e.g., vibration).

In some aspects, the amount of power available to electronic devices may be limited. In such instances, the power consumption of the electronic devices may be concerned by selectively turning of, or otherwise adjusting the operation of the electronic device's I/O devices. Accordingly, the need exists for new techniques for adjusting the operation of I/O devices.

SUMMARY

The present disclosure addresses this need. According to one aspect of the disclosure, an electronic device is provided processor configured to: receive a biological signal of a user; detect whether the electronic device is attached to or detached from the user based on at least the biological signal; and control an I/O device operationally connected to the electronic device based on whether the electronic device is attached to or detached from the user.

According to another aspect of the disclosure, a method comprising: receiving, by an electronic device, a biological signal of a user of the electronic device; detecting, by the electronic device, whether the electronic device is attached to or detached from the user based on at least the biological signal; and controlling, by the electronic device, an input/output (I/O) device that is operationally connected to the electronic device based on whether the electronic device is attached to or detached from the user.

According to yet another aspect of the disclosure, a non-transitory computer-readable medium having instructions recorded thereon which when executed by a processor, cause the processor to: receive a biological signal of a user in an electronic device; detect whether the electronic device is attached to or detached from the user based on at least the biological signal; and control an I/O device operationally connected to the electronic device based on whether the electronic device is attached to or detached from the user.

BRIEF DESCRIPTION OF THE DRAWINGS

The above and other aspects, features and advantages of certain exemplary aspects of the present disclosure will be more apparent from the following description taken in conjunction with the accompanying drawings, in which.

Throughout the drawings, like reference numerals will be understood to refer to like parts, components, and structures.

DETAILED DESCRIPTION

Figure 1:
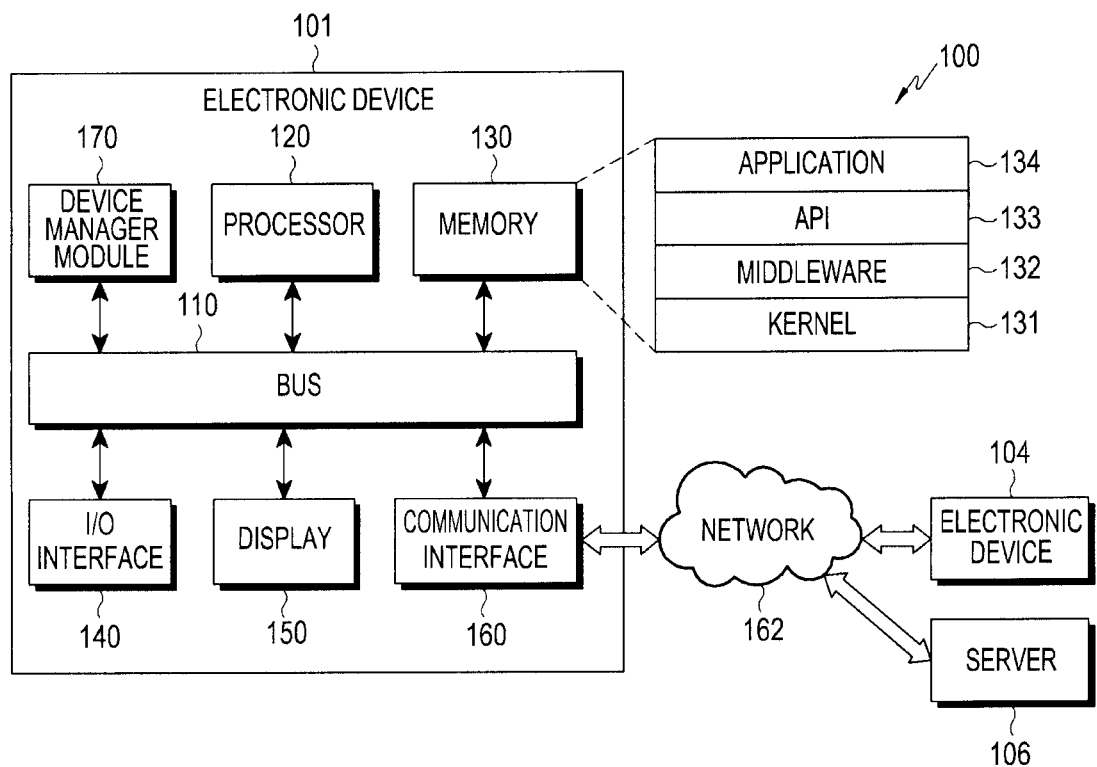
FIG. 1 is a diagram of an example of a network environment, according to aspects of the disclosure.

The following description provides various aspects of the present disclosure with reference to the accompanying drawings. It includes various specific details to assist in that understanding but these are to be regarded as merely exemplary and various modifications may be made to the aspects. The aspects of the disclosure may, however, be embodied in many different forms and should not be construed as limited to the aspects set forth herein; rather, these aspects are provided so that this disclosure will be thorough and complete, and will fully convey the scope of the aspects of the disclosure to those skilled in the art. Like numbers refer to like elements throughout.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "and/or" includes any and all combinations of one or more of the associated listed items. For examples, "A or B" may include A, or include B, or include both A and B.

It will be understood that, although the terms first, second, third, etc., may be used herein to describe various elements, components, regions, layers and/or sections, these elements, components, regions, layers and/or sections should not be limited by these terms. For example, these terms do not limit order and/or importance of corresponding elements, components, regions, layers and/or sections. These terms are only used to distinguish one element, component, region, layer or section from another region, layer or section. For example, a first user device and a second user device refer to two different user devices. Thus, a first element, component, region, layer or section discussed below could be termed a second element, component, region, layer or section without departing from the teachings of the aspects of the present disclosure.

When the term "connected" or "coupled" is used, a component may beg directly connected or coupled to another component or may be indirectly connected or coupled to another component via another new component.

However, if a component is said to be "directly connected" or "directly coupled" to another component, it should be interpreted as literally as it says. Furthermore, as used throughout the specification, the term operationally connected means "connected in a manner that permits signal to flow." Thus a first device is operationally connected to another device when the first device is connected to the other device in a manner that permits: (1) signal to flow from the first device to the second device, or (2) signal to flow from the second device, or (3) signal to flow from the first device to the second device or from the second device to the first device. In some implementations, two devices may be operationally connected when one of them is part of the other. The terminology used herein is for the purpose of describing particular aspects of the disclosure only and is not intended to be limiting in nature. It is to be understood that the singular forms "a," "an," and "the" include plural references unless the context clearly dictates otherwise.

Unless otherwise defined, all terms including technical and scientific terms used herein have the same meaning as commonly understood by one of ordinary skill in the art to which the aspects of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An electronic device according to various aspects of the present disclosure may include a biometrics functionality. For example, the electronic device may include at least one of smart phones, tablet Personal Computers (PCs), mobile phones, video phones, e-book readers, desktop PCs, laptop PCs, netbook computers, Personal Digital Assistants (PDAs), Portable Multimedia Players (PMPs), MP3 players, mobile medical devices, cameras, and wearable devices (e.g., Head-Mounted Devices (HMDs), such as electronic glasses, electronic clothes, electronic bracelets, electronic necklaces, electronic appcessories, electronic tattoos, or smart watches).

In some aspects, the electronic device may be a smart home appliance having the biometrics functionality. The smart home appliance may include at least one of e.g., televisions, Digital Video Disc (DVD) players, audio systems, refrigerators, air conditioners, cleaning machines, ovens, microwaves, washing machines, air purifiers, set-top boxes, TV sets (e.g., Samsung HomeSync™, Apple TV™, or Google TV™), game consoles, electronic dictionaries, electronic keys, camcorders, and electronic albums.

In some aspects, the electronic device may include at least one of a variety of medical equipment (e.g., Magnetic Resonance Angiography (MRA), Magnetic Resonance Imaging (MRI), Computed Tomography (CT), photographing device, ultrasonic device, etc.), navigation devices, Global Positioning System (GPS) receivers, Event Data Recorders (EDRs), Flight Data Recorders (FDRs), car infotainment devices, marine electronic devices (e.g., marine navigation systems, gyro-compass, etc.), avionics, security devices, car head units, industrial or home robots, banking agency's Automatic Teller Machines (ATMs), or Point of Sales (POSs) for shops.

In some aspects, the electronic device may include at least one of furniture or building/part of a structure including a biometrics functionality, electronic boards, electronic signature receiving devices, projectors, or various instrumental equipment (e.g., meters for water, electricity, gas, or radio waves). The electronic device in accordance with various aspects of the present disclosure may be one or more combinations of the aforementioned devices. In addition, the electronic device in accordance with various aspects of the present disclosure may be a flexible device. It will be obvious to a person of ordinary skill in the art that the electronic device is not limited to the aforementioned examples.

An electronic device in accordance with various aspects of the present disclosure will now be described with reference to accompanying drawings. The term 'user' as herein used may refer to a person who uses the electronic device or a device (e.g., an artificially intelligent device) that uses the electronic device.

FIG. 1 illustrates an example of a network environment 100 including an electronic device 101, according to aspects the present disclosure. Referring to FIG. 1, the electronic device 101 may include a bus 110, a processor 120, a memory 130, an input/output (I/O) interface 140, a display 150, a communication interface 160, and a device manager module 170.

The bus 110 may be a circuitry for interconnecting the enumerated components and delivering communications (e.g., control messages) among them.

The processor 120 may include processor (e.g., processing circuitry), such as an ARM-based processor, an x86 processor, a Field-Programmable Gate Array (FPGA), an Application-Specific Integrated Circuit, and/or any other suitable type of processor. The processor 120 may, for example, receive requests or commands from the enumerated components, the memory 130, the I/O interface 140, the display 150, the communication interface 160, or the device manager module 170 via the bus 110, interpret the requests or commands, and perform an operation or data processing according to the interpreted requests or commands.

The memory 130 may store requests, commands, or data received or generated from the enumerated components, e.g., the processor 120, the I/O interface 140, the display 150, the communication interface 160, or the device manager module 170. The memory 130 may include, for example, programming modules, such as kernel 131, middleware 132, Application Programming Interface (API) 133, application 134, or the like. Each of the programming modules may be implemented in software, firmware, hardware, or two or more combinations thereof.

The kernel 131 may control or manage system resources (e.g., the bus 110, the processor 120, the memory 130 or the like) to be used to carry out an operation or function implemented by the other programming modules, e.g., the middleware 132, the API 133, or the application 134. Furthermore, the kernel 131 may provide an interface for the middleware 132, the API 133, or the application 134 to access respective components of the electronic device 101 to control or manage them.

The middleware 132 may act as intermediary for the API 133 or the application 134 to communicate data with the kernel 131. In addition, the middleware 132 may perform control operations (e.g., scheduling or load balancing) in response to a task request received from the application 134 by way of e.g., placing a high priority on at least one application included in the application 134 to use system resources (e.g., the bus 110, the processor 120, the memory or the like) of the electronic device 101.

The API 133 is an interface for the application 134 to control a function provided from the kernel 131 or the middleware 132, and may include at least one interface or function (e.g., an instruction) for e.g., file control, window control, image processing, text control, etc.

In accordance with various aspects, the application 134 may include a Short Message Service (SMS)/Multimedia Message Service (MMS) application, an email application, a calendar application, an alarm application, a healthcare application (e.g., an application for measuring quantity of motion or blood sugar), or environmental information application (e.g., an application for providing atmospheric pressure, humidity, or temperature). Additionally or alternatively, the application 134 may be an application involved in information exchange between the electronic device 101 and an external electronic device 104. The application involved in such information exchange may include e.g., a notification relay application for relaying particular information to the external electronic device 104 or a device management application for managing the external electronic device 104.

For example, the notification relay application may include functionality for notifying the external electronic device 104 of notification information generated in any other application (e.g., the SMS/MMS application, the email application, the healthcare application, or the environmental information application) of the electronic device 101. Additionally or alternatively, the notification relay application may, for example, receive the notification information from the external electronic device 104 and provide the notification information to the user. The device manager application may manage (e.g., install, delete or update) a function (e.g., turning on/off the external electronic device 104 itself or a part of the external electronic device 104, or controlling display brightness of the external electronic device 104) with respect to part of the external electronic device 104 in communication with the electronic device 101, or a service (e.g., calling or messaging service) provided by the external electronic device 104 or an application running in the external electronic device 104.

In accordance with various aspects of the present disclosure, the application 134 may include an application designated depending on an attribute of the electronic device 104, e.g., on a type of the electronic device 104. For example, in case the external electronic device 104 is an MP3 player, the application 134 may include an application related to music replay. Similarly, in case the external electronic device 104 is a mobile medical device, the application 134 may include an application related to healthcare. In accordance with aspects of the disclosure, the application 134 may include at least one of an application dedicated to the electronic device 101, and an application received from the external electronic device 104 or a server 106.

The I/O interface 140 may deliver instructions or data entered by the user through the I/O device (e.g., a sensor, a keyboard, a communication module (e.g., a Bluetooth (BT) module, Wireless Fidelity (Wi-Fi) module) or a touch screen) to the processor 120, the memory 130, the communication interface 160, or the device manager module 170 via the bus 110. For example, the I/O interface 140 may provide data for a user touch input through the touch screen to the processor 120. The I/O interface 140 may also output a command or data received from the processor 120, the memory 130, the communication interface 160, or the device manager module 170 via the bus 110 through the I/O device (e.g., a speaker or the display 150). For example, the I/O interface 140 may output sound data processed by the processor 120 to the user.

The display 150 may display various information (e.g., multimedia data or text data) for the user.

The communication interface 160 may connect communication between the electronic device 101 and the external electronic device 104 or the server 106. For example, the communication interface 160 may be connected to a network 162 through wired or wireless communication and may communicate with the external electronic device 104 or the server 106. The wireless communication may include at least one of Wi-Fi, BT, Near Field Communication (NFC), GPS, or cellular communication (e.g., LTE, LTE-A, CDMA, WCDMA, UMTS, Wibro or GSM). The wired communication may include at least one of e.g., Universal Serial Bus (USB), High Definition Multimedia Interface (HDMI), Recommended Standard (RS) 232 or Plain Old Telephone Service (POTS).

In accordance with aspects of the disclosure, the network 162 may be a telecommunications network. The telecommunications network may include at least one of computer network, Internet, local area network (LAN), a wide area network (WAN), a cellular network, a telephone network, and/or any other suitable type of network. In accordance with aspects of the disclosure, a protocol (e.g., a transport layer protocol, a data link layer protocol or a physical layer protocol) for communication between the electronic device 101 and the external device 104 or the server 106 may be supported by at least one of the application 134, the API 133, the middleware 132, the kernel 131 or the communication interface 160.

The device manager module 170 may be operationally connected to other components (e.g., the processor 120, the memory 130, the I/O interface 140, or the communication interface 160) and obtain a surrounding situation of the electronic device (e.g., attachment or detachment of the electronic device 101 to or from the user). The device manager module 170 may also independently control a plurality of I/O devices (e.g., a sensor, a touch panel, a microphone, a speaker, the display 150, or the like) through the I/O interface 140 based on the surrounding situation of the electronic device 101. The device manager module 170 will be further described in connection with FIGS. 2 to 6.

Figure 2:
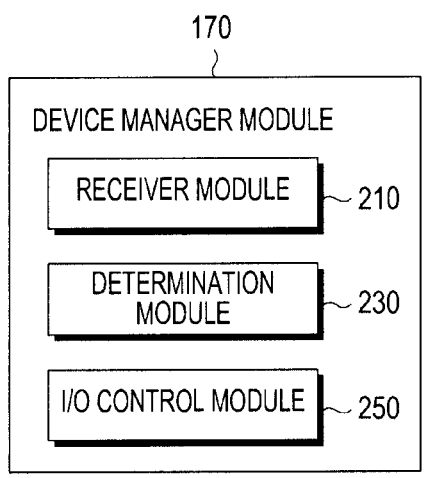
FIG. 2 is a block diagram of an example of a device manager, according to aspects of the disclosure.

FIG. 2 is a block diagram of an example of the device manager module 170 of the electronic device 101 in accordance with an aspect of the present disclosure. Referring to FIG. 2, the device manager module 170 may include a receiver module 210, a determination module 230, and I/O control module 250. Each of the modules may be implemented using hardware (e.g., one or more electronic circuits), software, and/or a combination of hardware and software.

The receiver module 210 may obtain at least one of biological signals of a user of the electronic device or various information associated with the electronic device 101 (e.g., motion information, information regarding brightness around the electronic device, status information of the electronic device, etc.).

In accordance with aspects of the disclosure, the receiver module 210 may receive a biological signal of the user with respect to the electronic device 101. For example, the receiver module 210 may directly obtain (or sense) a biological signal generated from the user with respect to the electronic device 101. Alternatively, the receiver module 210 may indirectly obtain a biological signal of the user obtained from an external device (e.g., the external electronic device 104 or the server 106).

The biological signal may include a signal corresponding to at least one of electrocardiogram (ECG), heart rate, heart rate variability (HRV), fingerprint, iris, body fat, oxygen saturation, pulse, skin hydration, skin hydration index, blood vessel information, face image, voice sample, image of an eye, image of lines of the palm, vein, electromyogram or brain waves. To receive such various biological signals, the receiver module 210 or the external device may include, for example, a ECG sensor or electrocardiography (EKG) sensor, a heartbeat sensor (e.g., a photoplethysmography (PPG) sensor, a heart rate monitor (HRM) sensor, or a heart rate variability (HRV) sensor), a fingerprint sensor, an iris sensor, a body fat measurement sensor, an oxygen saturation sensor, a temperature sensor, a skin hydration measurement sensor, a skin hydration index measurement sensor, a facial recognition sensor, a palm line recognition sensor, a vein recognition sensor, a electromyogram sensor or brain wave measurement sensor, and/or any other suitable type of sensor.

In accordance with aspects of the disclosure, the receiver module 210 may obtain a blood flow rate of the user through a photoplethysmography sensor. The receiver module 210 may measure a change in blood flow rate through the photoplethysmography sensor for a predetermined time (e.g., about 1 minute). The photoplethysmography sensor may obtain biological information regarding e.g., a heartbeat rate, a HRV or an ECG, based on the change in blood flow rate. In accordance with aspects of the disclosure, the receiver module 210 may obtain an electroencephalogram (EEG) signal as biological information through a brain wave measurement sensor. In accordance with aspects of the disclosure, the receiver module 210 may obtain an ECG signal as at least a part of the biological information through an ECG measurement sensor.

In accordance with aspects of the disclosure, the receiver module 210 may obtain at least one of the electronic device's motion information, an event, status information of the electronic device, surrounding environment information or information regarding a distance between the electronic device and an external device in communication with the electronic device. For example, the receiver module 210 may directly obtain the at least one information. Alternatively, the receiver module 210 may indirectly obtain the at least one information from the external device (e.g., the external electronic device or the server 106).

In accordance with aspects of the disclosure, the receiver module 210 may obtain the electronic device's motion information (e.g., moving distance, moving direction, rotation angle, etc.) through a motion sensor (e.g., an acceleration sensor, a gyro sensor, a geomagnetic sensor, a GPS module, etc.) operationally connected to the electronic device or the external device. The receiver module 210 may also obtain an event that has occurred in the electronic device or the external device. For example, the event may include an incoming call event, a message reception event, an alarm event, a calendar notification event, or a Social Network Service (SNS) event.

In accordance with aspects of the disclosure, the receiver module 210 may obtain information regarding the status of the electronic device. The status information of the electronic device may include, e.g., power state information (e.g., an indication of a remaining battery charge) or information about throughput of a processor included in the electronic device. In accordance aspects of the disclosure, the receiver module 210 may obtain surrounding environment information of the electronic device (e.g., the electronic device 101). The surrounding environment information may include, for example, information regarding brightness of the surroundings of the electronic device, sound information regarding sound generated in the surroundings of the electronic device (e.g., intensity, frequency, or wavelength of the sound), odor information or position information.

In accordance with aspects of the disclosure, the receiver module 210 may obtain information regarding a distance between the electronic device 101 and the external device (e.g., the external electronic device 104 or the server 106) in communication with the electronic device 101. For example, the receiver module 210 may obtain the information regarding the distance between the electronic device 101 and the external device (e.g., the external electronic device 104 or the server 106) in communication with the electronic device 101 based on a signal strength of a communication signal transmitted to communicate with the external device. For example, if the signal strength of the communication signal corresponds to a first predetermined range (e.g., stronger than a predetermined strength), the receiver module 210 may determine that the distance between the electronic device and the external device to be a first predetermined distance (e.g., a distance nearer than a reference distance for intercommunication). If the signal strength of the communication signal corresponds to a second predetermined range (e.g., weaker than a predetermined strength), the receiver module 210 may determine the distance between the electronic device and the external device to be a second predetermined distance (e.g., a distance farther than the reference distance).

The determination module 230 may determine whether the electronic device is attached to or detached from the user (or an attachment/detachment state) based on at least a biological signal (e.g., based on whether a biological signal is detected or not, information regarding an attribute of a biological signal (e.g., signal strength of the biological signal, a signal pattern of the biological signal, etc.), etc.). Thus, by way of example, in some implementations, the device may be considered attached to a user if the device is able to read one or more predetermined biometrics (e.g., heart rate, etc.) of the user. The attachment/detachment state may include, for example, detached state (or non-wearing state), attached state (or wearing state), or incompletely attached state (or incomplete wearing state). The detached state may include a state where the electronic device is detached from the user's body. The attached state may include a state where the electronic device is normally attached to the user's body. The incompletely attached state may include a state where the electronic device is abnormally attached to the user's body. In accordance with some aspects of the present disclosure, the attachment/detachment state (e.g., attachment, detachment, or incomplete attachment) may be defined or set in other various ways by user settings or by a designer of the electronic device.

In accordance with aspects of the disclosure, the electronic device may determine the attachment/detachment state of the electronic device based on whether a biological signal is detected. The electronic device may be, for example, a smart watch. If the smart watch is not worn on the wrist of the user (e.g., instead, the smart watch is put in a pocket of a garment that the user wears or in a bag the user carries, or the smart watch is located in an object (e.g., desk) other than the user's body), any biological signal of the user is not detected by the smart watch and thus the determination module 230 may determine that the smart watch is detached from the user.

On the other hand, if the smart watch is normally worn on the wrist of the user, a biological signal of the user is normally detected (e.g., in a certain signal pattern or at a strength enough to identify the biological signal) and thus the determination module 230 may determine that the smart watch is attached to the user. If the smart watch is abnormally (e.g., loosely) worn on the wrist of the user, a biological signal of the user may be detected incompletely (e.g., a signal strength or pattern of the detected biological signal is unstable) and thus the determination module 230 may determine that the smart watch is incompletely attached to the user. In another example, if the receiver module 210, e.g., a fingerprint sensor fails to detect a fingerprint of the user, the determination module 230 may determine that the electronic device is detached. If the receiver module 210 detects a fingerprint of the user, the determination module 230 may determine that the electronic device is attached.

In accordance with aspects of the disclosure, the determination module 230 may determine whether the electronic device is attached or detached based on the signal strength of a biological signal. The determination module 230 may determine that the electronic device is attached, if the signal strength of a biological signal corresponds to a first predetermined range (e.g., greater than a first strength). The determination module 230 may determine that the electronic device is detached, if the signal strength of a biological signal corresponds to a second predetermined range (e.g., weaker than a second strength). The determination module 230 may determine that the electronic device is incompletely attached, if the signal strength of a biological signal corresponds to a third predetermined range (e.g., weaker than the first strength but greater than the second strength).

For example, a pulse signal obtained through the receiver module 210, e.g., a heartbeat sensor may correspond to any of first to third predetermined ranges depending on whether the electronic device is attached, detached, or incompletely attached. A pulse signal received from a PPG sensor may include at least one of an AC component (a pulsating component) and a DC component. The AC component appears due to contraction and relaxation of the heart, and the DC component appears based on absorption or reflectance of a living body. For example, if a range of DC levels to which a received light signal corresponds is from about 0 as a minimum level up to about 200,000 as a maximum level, the pulse signal received may correspond, for example, to less than about 60,000 level (e.g., as the first predetermined range for the detached state), more than about 80,000 level (e.g., as the second predetermined range for the attached state), or more than about 60,000 but less than about 80,000 level (e.g., as the third predetermined range for the incompletely attached state). Since the DC level may be distinguished through amplification of a received signal, the range may vary depending on amplification range settings. Furthermore, even in the detached state, the DC level may become high due to the ambient light, and thus a DC level obtained after cancellation of components of the received ambient light may be used. In another example, the determination module 230 may determine whether the electronic device is attached, detached, or incompletely attached based on a range corresponding to current signal strength of a pulse signal obtained through the receiver module 210. For example, if a measured DC level corresponds to a range between about 30% and 50% of a maximum value that the receiver module 210 may measure, the determination module 230 may determine that the electronic device is detached. For this, one or more of an average DC level, a maximum DC level, and a minimum DC level detected for a predetermined period of time may be used.

In accordance with aspects of the disclosure, the determination module 230 may determine whether the electronic device is attached, detached, or incompletely attached, based on amplitude of pulse components of a biological signal. The amplitude of pulse components may include one or more of an amplitude of the R wave measured by an ECG sensor, an amplitude of the peak of AC components measured by a PPG sensor, or an amplitude of accelerated plethysmo. As an example, if an amplitude of an AC signal corresponding to a biological signal received through the receiver module 210 satisfies a predetermined condition (e.g., if the amplitude is about 20% to 60% of a predefined maximum amplitude), it indicates that fluctuations of light on a light receiving side is small due to vasodilation (increase in blood amount) in a heart contraction phase and vasoconstriction (decrease in blood amount) in a heart relaxation and thus the determination module 230 may determine that the electronic device is incompletely attached. For example, since an amplitude of an AC signal close to 0% of the predefined maximum amplitude means that there is almost no vasodilation and vasoconstriction, the amplitude of 20% of the predefined maximum amplitude may lead to a determination that the corresponding sensor is covered with a thing other than a living body or is significantly affected by ambient light (e.g., that the electronic device is in a detached state). Accordingly, if an amplitude of the AC signal exceeds 60% of the predefined maximum amplitude, it is determined that the electronic device is in an attached state. In another example, with a pulse signal received through a PPG sensor including both AC and DC components, if the DC component is close to the maximum level and the AC component(s) is as weak as under a predefined value, it is determined that only the DC component is strong while the AC component(s) is weak. Therefore, in this case, a great amount of light received at the PPG sensor is not determined as actual measurement of reflected or transmitted light of a vessel, and thus the electronic device is determined to be in the detached state.

In accordance with aspects of the disclosure, the determination module 230 may determine whether the electronic device is attached, detached, or incompletely attached, based on Signal-to-Noise Ratio (SNR) of a biological signal. With respect to a received pulse signal, if an SNR of a received light signal exceeds a threshold (e.g., about −8 dB) for a predetermined period of time, the electronic device is determined as being normally attached to the user; otherwise, the electronic device is determined as incompletely attached or detached from the user.

In accordance with aspects of the disclosure, the determination module 230 may determine whether the electronic device is attached, or incompletely attached, based on a signal pattern (e.g., a frequency or cycle) of a biological signal. The determination module 230 may compare a signal pattern of a biological signal received through the receiver module 210 with a predefined or pre-stored signal pattern. The predefined signal pattern may be based on, any suitable type of biometric that is indicated by the biological signal (e.g., fingerprint, brain wave, pulse, heartbeat, or the like).

If an extent of similarity or correspondence of the signal pattern of the biological signal and the predefined signal pattern corresponds to a first predetermined range (e.g., less than a first similarity), the determination module 230 may determine that the electronic device is detached from the user. If the extent of similarity or correspondence of the signal pattern of the biological signal and the predefined signal pattern corresponds to a second predetermined range (e.g., greater than a second similarity), the determination module 230 may determine that the electronic device is attached to the user. If the extent of similarity or correspondence of the signal pattern of the biological signal and the predefined signal pattern corresponds to a third predetermined range (e.g., greater than the first similarity but less than the second similarity), the determination module 230 may determine that the electronic device is incompletely attached to the user.

More specifically, the determination module 230 may compare a signal pattern of an ECG signal obtained through the receiver module 210, e.g., an ECG sensor with a predefined signal pattern. In the case of the ECG signal, the predefined signal pattern may include a pattern of a signal corresponding to a heart activity current, e.g., the P, Q, R, S, or T wave. In a case of a brain wave signal, the predetermined signal pattern may include a pattern of an electric signal generated from a cranial nerve, e.g., delta wave (about 0.2 to 0.4 Hz), a theta wave (about 4 to 8 Hz), an alpha wave (about 8 to 13 Hz), a beta wave (about 13 to 30 Hz), or a gamma wave (about 30 to 50 Hz).

If the degree of similarity between the signal pattern of the ECG signal and the predefined signal pattern is higher than a first threshold (e.g., about more than 70% similarity) or the same as the first threshold, the determination module 230 may determine that the electronic device is attached to the user. If the degree of similarity between signal pattern of the ECG signal and the predefined signal pattern is lower than a first threshold (e.g., about less than 30% similarity), the determination module 230 may determine that the electronic device is detached from the user. If the degree of similarity between the signal pattern of the ECG signal and the predefined signal pattern is greater than the first threshold and less than a second threshold, (e.g., within a range about 30% to 70% similarity), the determination module 230 may determine that the electronic device is incompletely attached to the user.

In accordance with aspects of the disclosure, the determination module 230 may determine further information regarding the attachment/detachment state of the electronic device (e.g., information regarding whether or not the user carries the electronic device) based on motion of the electronic device. For example, the determination module 230 may further determine a possession state of the electronic device, i.e., whether the user carries the electronic device in the detached state, e.g., whether the electronic device is put in a bag the user carries (or a pocket of the user's garment), or whether the electronic device is located on an object (e.g., a desk) far from the user.

The possession state may include, for example, a state where the electronic device is not attached to or worn on a body part (e.g., the wrist in case the electronic device is a smart watch) of the user but is located in another body part (e.g., the palm) of the user. The body part for the electronic device to be attached to may depend on types of the electronic device; for example, in case of the smart watch, the body part may be the wrist of the user and in case of a Head Mount Device (HMD), the body part may be the head of the user. The possession state may also include, e.g., a state where the electronic device is put in a pocket of the garment of the user, or a state where the electronic device is put in a bag the user carries. A non-possession state may be determined by the determination module 230 when the electronic device is located in a place (e.g., on a table) not affected by the user's motion.

In accordance with aspects of the disclosure, the determination module 230 may determine the possession state of the electronic device based on a motion intensity of the electronic device. For example, if the motion intensity corresponds to a first predefined range (e.g., stronger than a predefined intensity), the determination module 230 may determine that the electronic device is possessed by the user (or located in a transportation means). If the motion intensity corresponds to a second predefined range (e.g., weaker than the predefined intensity), the determination module 230 may determine that the electronic device is not in the user's possession.

In accordance with another aspect, the determination module 230 may determine the possession state of the electronic device based on a signal pattern of a motion of the electronic device. For example, the determination module 230 may determine whether the user possesses the electronic device based on similarity between a pattern of a signal corresponding to a motion and a predefined pattern. The predefined pattern may include data patterns (e.g., velocity, acceleration, or shaking degrees) corresponding to various motions of the user, such as walking motion, running motion, etc. The predefined pattern may also include data information corresponding to various transportation means (e.g., walking, travelling by car, etc.).

In accordance with aspects of the disclosure, the determination module 230 may authenticate or identify the user based on at least one of the biological signal or the motion of the electronic device. For example, with the biological signal for user authentication, a memory, such as the memory 130 operationally connected to the electronic device may store a first biological signal for a first user and a second biological signal for a second user. If a biological signal received through the receiver module 210 corresponds to the first biological signal, the determination module 230 may determine that the user of the electronic device is the first user. If a biological signal received through the receiver module 210 corresponds to the second biological signal, the determination module 230 may determine that the user of the electronic device is the second user.

In another example, if the biological signal is iris information (e.g., a signal that identifies a characteristic of an iris of the user of the electronic device), the determination module 230 may compare iris information obtained through the receiver module 210 with predefined iris information for respective users. If the iris information obtained matches one among the predefined iris information for respective users, the determination module 230 may determine that a user corresponding to the matched predefined iris information is the user of the electronic device.

In another example, in case of using a motion for user authentication, a memory, such as the memory 130 operationally connected to the electronic device may store first motion information for a first user and second motion information for a second user. If motion information received through the receiver module 210 corresponds to the first motion information, the determination module 230 may determine that the user of the electronic device is the first user. If motion information received through the receiver module 210 corresponds to the second motion information, the determination module 230 may determine that the user of the electronic device is the second user.

For example, if the motion information is generated as a result of the user walking, the determination module 230 may compare the motion information through the receiver module 210 with one or more walking information samples that are associated with different users. If the motion information obtained matches one of the samples, the determination module 230 may determine that the sample's respective user is the user of the electronic device.

In accordance with aspects of the disclosure, the determination module 230 may determine importance of an event obtained through the receiver module 210. The determination module 230 may assign importance degrees (e.g., priorities) to respective events. The importance degrees (e.g., priorities) may be assigned based on a type (or degree of urgency) of the event for the user. For example, an incoming call event may be assigned a first importance (e.g., high priority), a message reception event may be assigned second importance (e.g., priority lower than the first priority), and an alarm event a third importance (e.g., priority lower than the second priority). The importance degree may also be determined based on the urgency of a feature of an event. For example, if an event is generated as a result of a communication originated by an important person or indicates an emergency (e.g., a traffic accident, a fire, or the like), higher importance may be assigned to the event.

The I/O control module 250 may independently control a plurality of I/O devices operationally connected to the electronic device based on the attachment/detachment state of the electronic device. For example, based on the attachment/detachment state (including the attached state, the detached state, or the incompletely attached state) determined based on a biological signal or motion information, the I/O control module 250 may separately (or individually) control the plurality of I/O devices (including a microphone, display, speaker, or haptic device) to be turned on or off or separately (or individually) adjust the strength of I/O signals of the I/O devices.

In accordance with aspects of the disclosure, if the electronic device is determined to be detached from the user (e.g., if no biological signal is detected or a smart watch as the electronic device is determined to be put in a pocket of the user's garment or being located on an object (e.g., a desk) other than a body part of the user), the I/O control module 250 may turn off at least one of the I/O devices. For example, the electronic device may be a wearable device, such as a headphone- or earphone-type electronic device worn by a user, allowing the user to enjoy contents. If the electronic device is detached from the user, the I/O control module 250 may turn off the display to prevent at least a part of the content from being replayed or turn off the speaker to stop reproducing sound or turn off the haptic device to stop producing vibration.

In accordance with aspects of the disclosure, if the electronic device is determined to be normally attached to the user (e.g., if a biological signal is normally detected or the electronic device is determined as being correctly worn by the user), the I/O control module 250 may turn on at least one of the I/O devices. For example, the I/O control module 250 may turn on the display to replay video footage, turn on the speaker to reproduce sound or turn on the haptic device to produce vibration.

In accordance with aspects of the disclosure, if the electronic device is determined to be incompletely attached to the user (e.g., if a biological signal is abnormally detected or a the electronic device is determined to be being improperly (loosely) worn on the wrist of the user), the I/O control module 250 may independently control at least one of the I/O devices to provide a notification about the incompletely attached state to the user. For example, if a smart watch is not correctly worn by the user and thus the biological signal is not normally detected, the I/O control module 250 may provide the user with feedback information about the incompletely attached state. By way of example, the feedback information may include visual information provided through a display, sound information through provided through a speaker, vibration information provided through a haptic device, or odor information provided through an odor generation device. Abnormal detection of the biological signal received through the receiver module 210 may include one or the biological has an SNR less than a threshold. In accordance with aspects of the disclosure, the I/O control module 250 may output a message requesting to loosen or fasten the strap of the smart watch, as a part of the visual information.

In accordance with aspects of the disclosure, if the electronic device is determined to be detached from the user (e.g., if any biological signal is not detected or the electronic device is not worn by the user), the I/O control module 250 may independently control at least one of the I/O devices to provide a notification about the detached state to the user.

In accordance with aspects of the disclosure, when an output signal or an input signal is output or input through at least one of the plurality of I/O devices, the I/O control module 250 may independently control respective signal strength of the at least one I/O device based on the attachment/detachment state of the electronic device. For example, if a smart watch as an example of the electronic device is in the attached state, the I/O control module 250 may control brightness of the display to be 'high', the volume of the speaker to be 'low', or vibration strength of the haptic device to be 'medium'. On the other hand, if the electronic device is in the detached state, the I/O control module 250 may control brightness of the display to be 'low' or 'off', output intensity of the speaker to be 'high', or vibration intensity of the haptic device to be 'low'.

The I/O control module 250 may independently control the I/O devices further based on a motion of the electronic device. For example, if motion intensity of the electronic device is 'high' (e.g., when the user who carries or wears the electronic device is walking or running at a fast speed, the I/O control module 250 may independently control the I/O devices to provide strong output signals as compared with an occasion where motion intensity of the electronic device is 'low' (e.g., when the user who carries or wears the electronic device is walking slowly or moving slightly). For example, the I/O control module 250 may control vibration intensity of the haptic device to be 'high' for 'high' motion intensity; 'medium' for 'medium'; 'low' for 'low'.

In accordance with aspects of the disclosure, the I/O control module 250 may independently control a plurality of I/O devices to provide notifications in response to an event, based on the motion of the electronic device. For example, if motion intensity of the electronic device is 'high', it is difficult to check information through the display, and thus, for an event of SNS message reception, the I/O control module 250 may control the speaker or the haptic device to produce a sound or vibration corresponding to a notification about the SNS message reception. On the other hand, if the motion intensity is 'low', the I/O control module 250 may provide a notification about the SNS message reception through the display.

In accordance with aspects of the disclosure, the I/O control module 250 may differently control the plurality of I/O devices, based on importance of an event that has occurred in the electronic device. For example, even when the motion intensity of the electronic device is 'high', if an attribute of a message received by the electronic device has high importance (e.g., content of the message is important or urgent, or a sender of the message is an important person for the user), the I/O control module 250 may turn on the display while controlling the speaker or the haptic device to produce louder sound or stronger vibration. On the other hand, even when the motion intensity of the electronic device is 'low', if the importance of a message is low (e.g., content of the message contains a blocked word or spam, or a sender of the message is unknown), the I/O control module 250 may turn off the display while controlling the speaker or the haptic device to produce weaker sound or weaker vibration.

In accordance with aspects of the disclosure, the I/O control module 250 may differently control the plurality of I/O devices for an event that contains time information. For example, for an alarm event, the I/O control module 250 may control the signal strength of at least one of I/O devices to become gradually stronger as a predefined time approaches. Furthermore, for example, for a certain event, the I/O control module 250 may only turn on the haptic device to produce vibration e.g., about 1 hour before the predefined time for the certain event. The I/O control module 250 may turn on both the haptic device and the speaker to produce both vibration and sound e.g., 2 hours before the predefined time for the certain event.

In accordance with aspects of the disclosure, the I/O control module 250 may control a plurality of I/O devices further based on applications running in the electronic device. For example, for an application running in the electronic device using a biological signal of the user (e.g., a stress measurement application), the I/O control module 250 may control the plurality of I/O devices not to run any other application or not to provide notifications corresponding to the other applications.

In another aspect, even while an application using a biological signal is running in the electronic device, if the importance of a message received by the electronic device is high, the I/O control module 250 may provide a notification of the message through at least one of the plurality of I/O devices. For example, the I/O control module 250 may turn on the display, lower the volume of the speaker, or lower the vibration intensity of the haptic device to provide the notification of the message.

In accordance with aspects of the disclosure, the I/O control module 250 may independently control a plurality of I/O devices based on information regarding a distance between the electronic device, such as the electronic device 101 and the external device (e.g., the external electronic device 104 or the server 106). For example, if it is determined that the distance between the electronic device and the external device is relatively close (e.g., if a smart watch as the electronic device and a cell phone as the external device is about 1 M distance away from each other), the I/O control module 250 may turn off at least one I/O device or decrease the respective signal strength of the plurality of I/O devices. On the other hand, if it is determined that the distance between the electronic device and the external device is relatively far from each other (e.g., if a smart watch as the electronic device and a cell phone as the external device is about 5 M distance away from each other), the I/O control module 250 may increase the respective signal strength of the plurality of I/O devices.

In accordance with aspects of the disclosure, the I/O control module 250 may adjust (or set) the respective signal strength of the plurality of I/O devices to be gradually stronger with increase in the distance between the electronic device and the external device. Furthermore, while an application for discovering an external device (e.g., device discovery application) is running in the electronic device, the I/O control module 250 may help the user find an external device by adjusting (or setting) the respective signal strength of the plurality of I/O devices corresponding to the external device.

In accordance with aspects of the disclosure, the I/O control module 250 may independently control the plurality of I/O devices, further based on status information of the electronic device. For example, if the remaining battery power of the electronic device is high (more than 60%), the I/O control module 250 may turn on the display that usually consumes more battery power, or control the haptic device or the speaker to produce stronger vibration or sound. On the other hand, if the remaining battery power of the electronic device is low (less than 30%), the I/O control module 250 may turn off the display, or control the haptic device or the speaker to produce weaker vibration or sound.

In accordance with aspects of the disclosure, the I/O control module 250 may independently control the plurality of I/O devices, based on user authentication information for the electronic device. For example, if the user of the electronic device is determined to be an adult, the I/O control module 250 may turn on a plurality of I/O devices individually and adjust the respective signal strength of the plurality of I/O devices depending on an extent to which the user controls the plurality of I/O devices. On the other hand, if the user of the electronic device is determined to be an adolescent, the I/O control module 250 may turn on at least one of the plurality of I/O devices and control the plurality of I/O devices to restrict the user in using the electronic device. In addition, the I/O control module 250 may control the plurality of I/O devices based not only on the user authentication information but also a type of content to be provided by the electronic device (e.g. for adults only or for children).

In accordance with aspects of the disclosure, the I/O control module 250 may control the plurality of I/O devices further based on surrounding information of the electronic device (e.g., brightness information, sound information, odor information, or position information of the surroundings of the electronic device). For example, if the surroundings of the electronic device are relatively quiet, the I/O control module 250 may turn the volume of the speaker down because the user may sense weak sound from the speaker. On the other hand, if the surroundings of the electronic device are noisy, the I/O control module 250 may turn the volume of the speaker up (e.g., to be stronger than the surrounding noise). Alternately, if the surroundings of the electronic device are noisy, the I/O control module 250 may turn on the haptic device to produce vibration for the user just in case the user might not be able to catch even the stronger sound from the speaker.

Furthermore, if an odor or fragrance fumed from the surroundings of the electronic device is weak, the I/O control module 250 may control the odor generation device to produce a weak fragrance because the user may sense even the weak fragrance. On the other hand, if an odor or fragrance fumed from the surroundings of the electronic device is strong, the I/O control module 250 may control the odor generation device to produce a strong fragrance (e.g, stronger than the surrounding odor or fragrance).

In accordance with aspects of the disclosure, the I/O control module 250 may determine setting information for each of the plurality of I/O devices based on the attachment/detachment state, in order to independently control the plurality of I/O devices depending on at least the attachment/detachment state of the electronic device. The setting information may include, for example, information about how to execute each of the plurality of I/O devices operationally connected to the electronic device. For example, the setting information may include turn-on/turn-off information for each of the plurality of I/O devices, strength information for respective input signals input through the plurality of I/O devices, strength information for respective output signals output through the plurality of I/O devices, or the like. In case the electronic device is detached from the user, the I/O control module 250 may determine setting information to turn off the display, set the speaker volume to be high, set the vibration strength of the haptic device to be low.

In accordance with aspects of the disclosure, the I/O control module 250 may independently control the plurality of I/O devices, further based on setting information set by the user for the plurality of I/O devices. For example, with the electronic device being detached from the user, which requires the display to be turned off, if the user sets the display to be turned on all the time, the I/O control module 250 may turn on the display.

While in the aspects of the present disclosure displays, speakers, haptic devices or odor generation devices have been discussed as a plurality of I/O devices, aspects of the present disclosure are not limited thereto. Furthermore, while in the aspects of the present disclosure predefined ranges for various information (e.g., motion information or status information of the electronic device) have been discussed to determine the attachment/detachment state of the electronic device, the ranges are not limited thereto but may be implemented by user setting information or a designer of the electronic device to have other various predefined ranges. The plurality of I/O devices operationally connected to the electronic device may include I/O devices contained in the electronic device, such as the electronic device 101 or I/O devices contained in the external device, such as the external electronic device 104 or the server 106 in communication with the electronic device.

In accordance with various aspects, an electronic device, such as the electronic device 101 for controlling a plurality of I/O devices may include a receiver module, such as the receiver module 210 for receiving a biological signal (e.g., a pulse signal) of a user, a determination module, such as the determination module 230 for determining whether the electronic device is attached to or detached from the user, based on at least the biological signal (e.g., signal strength, pattern, amplitude of AC component(s) of the pulse signal); and an I/O control module, such as the I/O control module 250 for independently controlling the plurality of I/O devices operationally connected to the electronic device (e.g., for independently controlling the speaker and the haptic device to produce louder sound and to be turned off, respectively), based on whether the electronic device is attached or detached.

In accordance with various aspects, the receiver module may obtain at least one of electrocardiogram (ECG), heart rate, heart rate variability (HRV), fingerprint, iris, body fat, oxygen saturation, pulse, skin hydration, skin hydration index, blood vessel information, face, voice, eye, lines of the palm, vein, electromyogram or brain waves, as the biological signal.

In accordance with various aspects, the determination module obtains attribute information (e.g., signal strength or signal pattern) of the biological signal, determines the electronic device is attached to the user if the attribute information corresponds to a first predefined range, determines the electronic device is detached from the user if the attribute information corresponds to a second predefined range, and determines the electronic device is incompletely attached to the user if the attribute information corresponds to a third predefined range.

In accordance with various aspects, the determination module may authenticate the user by using at least one of the biological signal or motion information of the electronic device. For example, with the biological signal being fingerprint information, the determination module may determine the user as a first user if the fingerprint information corresponds to first fingerprint information; and may determine the user as a second user if the fingerprint information corresponds to second fingerprint information.

In accordance with various aspects, the determination module obtains signal strength of the biological signal, determines the electronic device is attached to the user if the signal strength corresponds to a first predefined range, and determines the electronic device is detached from the user if the signal strength corresponds to a second predefined range.

In accordance with various aspects, the determination module may determine the electronic device is incompletely attached to the user if the signal strength corresponds to a third predefined range.

In accordance with various aspects, the I/O control module may control at least one of the plurality of I/O devices to notify the user of the incompletely attached state or the detached state of the electronic device, if the electronic device is incompletely attached to the user or detached from the user.

In accordance with various aspects, the determination module may determine an application (e.g., a stress measurement application) running in the electronic device.

In accordance with various aspects, the I/O control module may control the plurality of I/O devices further based on the application (e.g., the I/O control module may control the I/O devices not to run any other application or not to provide notifications corresponding to any other application).

In accordance with various aspects, the I/O control module may determine setting information for each of the plurality of I/O devices based on whether the electronic device is attached or detached, and control one of the plurality of I/O devices based on the corresponding setting information (e.g., the I/O control module may control the haptic device among the speaker and the haptic device to produce high vibration).

In accordance with various aspects, the setting information may include at least one of turn-on/off information for each of the plurality of I/O devices and signal strength information about respective input or output signals input or output through the plurality of I/O devices.

In accordance with various aspects, the I/O control module may control each of the plurality of I/O devices to be turned on or off.

In accordance with various aspects, the plurality of I/O devices may include at least one of a speaker, a haptic device, an odor generation device, or a display, and the I/O control module may control at least one of volume of the speaker, vibration intensity of the haptic device, intensity of fragrance of the odor generation device, or brightness of the display.

In accordance with various aspects, the I/O control module may control signal strength of at least one of the plurality of I/O devices based on signal strength corresponding to information about surroundings of the electronic device (e.g., brightness information, noise information, odor information of the surroundings of the electronic device).

In accordance with various aspects, the I/O control module may control the plurality of I/O devices further based on at least one of status information of the electronic device, motion information of the electronic device, authentication information of the user, and information about a distance between the electronic device and an external device in communication with the electronic device.

In accordance with various aspects, the I/O control module may control the plurality of I/O devices further based on importance of an event obtained in the electronic device (e.g., importance of a message, degree of urgency, or importance of a sender of the message).

In accordance with various aspects, the I/O control module may control at least one of the plurality of I/O devices to provide notification information regarding the event based on the importance of the event.

Figure 3:
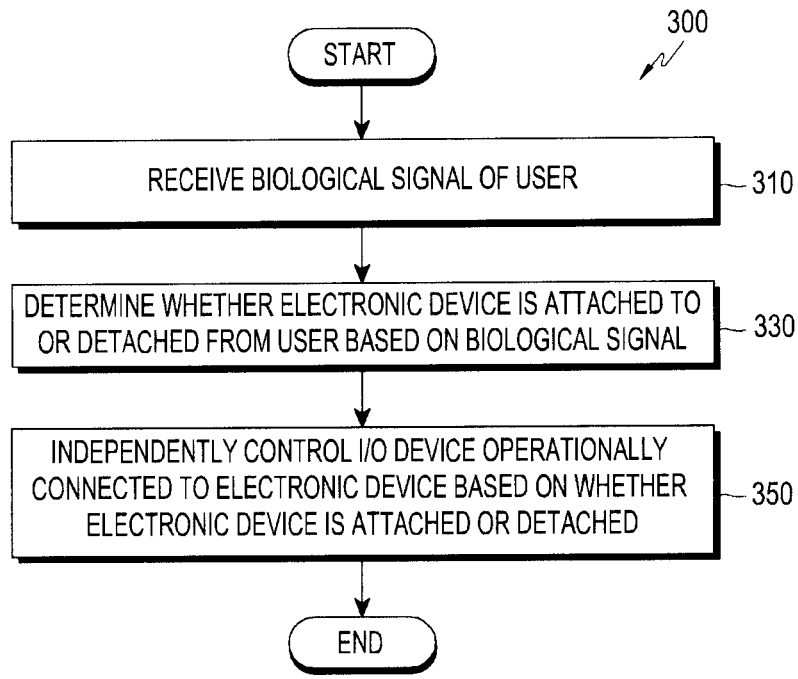
FIG. 3 is a flowchart of an example of a process for controlling a plurality of input/output (I/O) devices in an electronic device, according to aspects of the disclosure.

FIG. 3 is a flowchart of a process 300 for controlling a plurality of I/O devices in an electronic device, such as the electronic device 101, according to an aspect of the present disclosure. In operation 310, the electronic may receive a biological signal (e.g., a pulse signal) of a user. In accordance with aspects of the disclosure, the electronic device may further obtain at least one of motion information indicating a characteristic of movement of the electronic device, an indication of an event, status information of the electronic device, surrounding environment information or information regarding a distance between the electronic device and an external device in communication with the electronic device (herein collectively referred to as context information).

In operation 330, the electronic device may determine whether the electronic device is attached to or detached from a user (e.g., attachment/detachment state of the electronic device), based on at least one biological signal (e.g., signal strength of the pulse signal). In accordance with aspects of the disclosure, the electronic device may further determine detailed information regarding the attachment/detachment state of the electronic device (e.g., regarding whether or not the user carries the electronic device) based on the context information of the electronic device.

In operation 350, the electronic device (e may change the state of at least one of a plurality of I/O devices (e.g., a speaker, a display, a haptic device, and an odor generation device) operationally connected to the electronic device, based on at least the attachment/detachment state. For example, depending on at least the attachment/detachment state of the electronic device, the electronic device may power off the I/O device, increase the volume of sound output by the I/O device, increase brightness of the I/O device, change vibration strength of the I/O device, or change a fragrance intensity of the I/O device.

Figure 4:
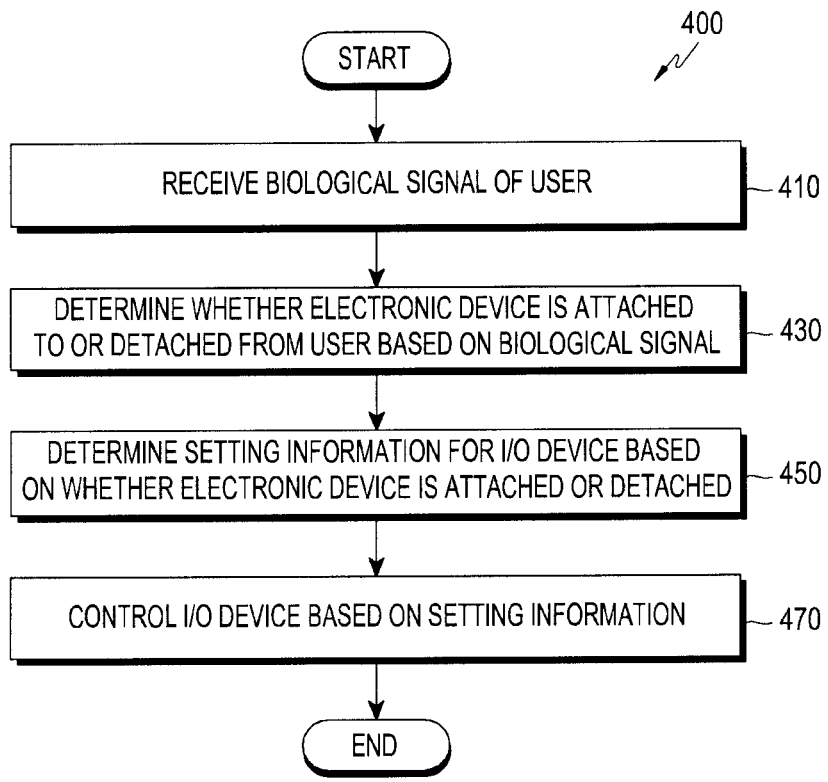
FIG. 4 is a flowchart of another example of a process for controlling a plurality of I/O devices in an electronic device, according to aspects of the disclosure.

FIG. 4 is a flowchart of a process 400 for controlling a plurality of I/O devices in an electronic device, such as the electronic device 101, according to another aspect of the present disclosure. Description of operations similar or identical to those of FIG. 3 will be omitted herein. In operation 410, the electronic device (may receive a biological signal (e.g., a brain wave signal) of a user.

In operation 430, the electronic device may determine whether the electronic device is attached to or detached from a user (e.g., attachment/detachment state of the electronic device), based on at least the biological signal (e.g., signal strength of the brain wave signal).

In operation 450, the electronic device may determine setting information for at least one of a plurality of I/O devices operationally connected to the electronic device based on at least attachment/detachment state of the electronic device. For example, the setting information may include turn-on/turn-off setting information, volume setting information, brightness setting information, and/or any other suitable type of setting information.

In operation 470, the electronic device may change the state of the at least one of the plurality of I/O devices based on the setting information. For example, if setting information for a display indicates 'turn off', setting information for a speaker indicates 'volume high', and setting information for a haptic device indicates 'weak vibration', the electronic device may turn off the display, turn the volume of the speaker up, and control the haptic device to produce weak vibration.

Figure 5:
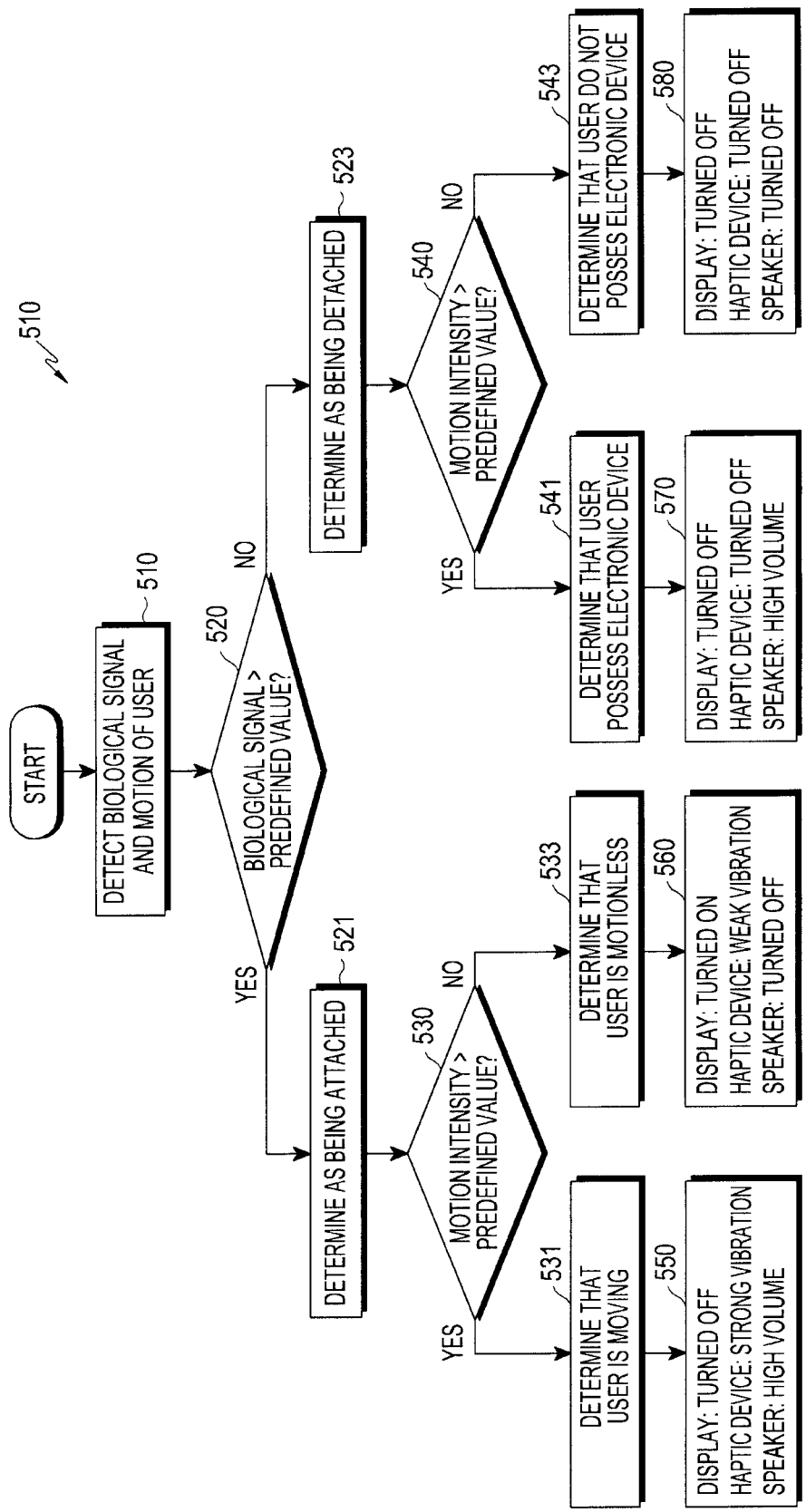
FIG. 5 is a flowchart of yet another example of a process for controlling a plurality of I/O devices in an electronic device, according to aspects of disclosure.

FIG. 5 is a flowchart of a process 500 for controlling a plurality of I/O devices, such as a display, a haptic device, and a speaker in an electronic device, such as the electronic device 101, according to another aspect of the present disclosure. In an aspect, the electronic device may independently control the plurality of different I/O devices operationally connected to the electronic device in various ways, based on various types of context information associated with the electronic device (e.g., a biological signal or motion of a user of the electronic device).

For example, in operation 510, the electronic device may detect a motion as one of the biological signal of the user for the electronic device and the context information of the electronic device. In operation 520 the electronic device may compare the biological signal of the user with a predefined value (e.g., a predefined reference associated with biological signals). For example, the electronic device may determine which range of a plurality of predefined ranges the strength of the biological signal belongs to. In operation 521, if the biological signal is greater than the predefined value, the electronic device may determine that the electronic device is attached to the user. On the other hand, in operation 523, if the biological signal is less than the predefined value, the electronic device (may determine that the electronic device is detached from the user.

In accordance with aspects of the disclosure, the electronic device (may determine further information regarding the state of the electronic device (e.g., information regarding motion or position of the electronic device) based on the attachment/detachment state of the electronic device and the motion of the electronic device. For example, in operations 530 and 540, the electronic device may compare a motion intensity of the electronic device with a predefined value (e.g., a predefined reference associated with motions), i.e., the electronic device may determine which range of a plurality of predefined ranges the motion intensity belongs to.

In accordance with aspects of the disclosure, with the electronic device being attached to the user, in operation 531, if the motion intensity is greater than the predefined value, the electronic device may determine that the electronic device is moving (e.g., that the user who carries the electronic device is intensely working out or walking violently). In operation 533, if the motion intensity is less than the predefined value, the electronic device may determine that the electronic device is motionless (e.g., in a case the user wearing the electronic device uses the stress measurement application).

In accordance with aspects of the disclosure, with the electronic device being detached from the user, in operation 541, if the motion intensity is greater than the predefined value, the electronic device may determine that the user carries the electronic device. For example, the electronic device may determine that the user carries the electronic device in a place where the electronic device is not supposed to be located (e.g., for a smart watch, if it is not worn on the wrist of the user but is put in a pocket of a garment worn by the user). In operation 543, if the motion intensity is less than the predefined value, the electronic device may determine that the user does not currently possess the electronic device (e.g., the electronic device is located on a desk not affected by the user's motion).

In accordance with aspects of the disclosure, the electronic device may control one or more of a display that is operationally connected to the electronic device, a haptic device that is operationally connected to the electronic device and a speaker that is operationally connected to the electronic device, based on the attachment/detachment state of the electronic device and a state of the electronic device determined by the motion (e.g., moving, motionless, possessed or non-possessed). For example, in operation 550, if the electronic device is carried by the user who is moving, the electronic device may turn off the display, control the haptic device to produce intense vibration, and turn the volume of the speaker up. In operation 560, if the electronic device is carried by the user who is motionless, the electronic device may turn on the display, control the haptic device to produce weak vibration, and turn off the speaker.

In operation 570, if the electronic device is detached from the user although possessed by the user, the electronic device may turn off the display, turn off the haptic device, and turn the volume of the speaker up. In operation 580, if the electronic device is detached from the user and is not possessed by the user, the electronic device may turn off the display completely, the haptic device, and the speaker.

In accordance with various aspects, a method for controlling a plurality of I/O devices may include receiving a biological signal (e.g., a brain wave signal) of a user in an electronic device, determining whether the electronic device is attached to or detached from the user based on at least the biological signal (e.g., a pattern of the brain wave signal), and independently controlling at least one of a plurality of I/O devices (e.g., a display or a microphone) operationally connected to the electronic device (e.g., independently controlling screen brightness of the display to be low or turning on the microphone), based on whether the electronic device is attached to or detached from the user.

In accordance with various aspect, receiving a biological signal of a user in an electronic device may include obtaining at least one of electrocardiogram (ECG), heart rate, heart rate variability (HRV), fingerprint, iris, body fat, oxygen saturation, pulse, skin hydration, skin hydration index, blood vessel information, face image, voice sample, eye image, an image of lines of the palm, or, electromyogram or brain waves, as the biological signal.

In accordance with various aspects, determining whether the electronic device is attached to or detached from the user based on at least the biological signal may include obtaining attribute information (e.g., signal strength or signal pattern) of the biological signal, determining the electronic device is attached to the user if the attribute information corresponds to a first predefined range, determining the electronic device is detached from the user if the attribute information corresponds to a second predefined range, and determining the electronic device is incompletely attached to the user if the attribute information corresponds to a third predefined range.

In accordance with various aspects, determining whether the electronic device is attached to or detached from the user based on at least the biological signal may include authenticating the user by using at least one of the biological signal or motion information of the electronic device. For example, authenticating the user by using at least one of the biological signal or motion information of the electronic device may include determining the user to be a first user if the motion information corresponds to first motion information, and determining the user to be a second user if the motion information corresponds to second motion information.

In accordance with various aspects, determining whether the electronic device is attached to or detached from the user based on at least the biological signal may include obtaining a signal strength of the biological signal, determining that the electronic device is attached to the user if the signal strength corresponds to a first predefined range, and determining that the electronic device is detached from the user if the signal strength corresponds to a second predefined range.

In accordance with various aspects, determining whether the electronic device is attached to or detached from the user based on at least the biological signal may include determining that the electronic device is incompletely attached to the user if the signal strength corresponds to a third predefined range.

In accordance with various aspects, independently controlling at least one of a plurality of I/O devices may include controlling at least one of the plurality of I/O devices to notify the user of the incompletely attached state or the detached state of the electronic device, if the electronic device is incompletely attached to the user or detached from the user.

In accordance with various aspects, determining whether the electronic device is attached to or detached from the user based on at least the biological signal may include determining an application (e.g., a stress measurement application) running in the electronic device.

In accordance with various aspects, independently controlling a plurality of I/O devices may include controlling the plurality of I/O devices independently further based on the application (e.g., controlling the I/O devices not to run any other application or not to provide notifications corresponding to any other application).

In accordance with various aspects, independently controlling a plurality of I/O devices may include determining setting information for each of the plurality of I/O devices based on whether the electronic device is attached to or detached from the user, and controlling one of the plurality of I/O devices based on the corresponding setting information (e.g., controlling a display among the display and a microphone to be turned on).

In accordance with various aspects, the setting information may include at least one of turn-on/off information for each of the plurality of I/O devices and signal strength information about respective input or output signals input or output through the plurality of I/O devices.

In accordance with various aspects, independently controlling a plurality of I/O devices may include turning off each of the plurality of I/O devices.

In accordance with various aspects, the plurality of I/O devices may include at least one of a speaker, a haptic device, an odor generation device, or a display, and independently controlling a plurality of I/O devices may include controlling at least one of volume of the speaker, vibration intensity of the haptic device, intensity of fragrance of the odor generation device, or brightness of the display.

In accordance with various aspects, independently controlling a plurality of I/O devices may include controlling signal strength of at least one of the plurality of I/O devices based on information about surroundings of the electronic device (e.g., brightness information, noise information, odor information of the surroundings of the electronic device).

In accordance with various aspects, independently controlling a plurality of I/O devices may include controlling the plurality of I/O devices further based on at least one of status information of the electronic device, motion information of the electronic device, authentication information of the user, and information about a distance between the electronic device and an external device in communication with the electronic device.

In accordance with various aspects, independently controlling a plurality of I/O devices may include controlling the plurality of I/O devices further based on importance of an event obtained by the electronic device (e.g., importance of a message, degree of urgency, or importance of a sender of the message).

In accordance with various aspects, independently controlling a plurality of I/O devices may include controlling at least one of the plurality of I/O devices (e.g., a haptic device among the haptic device and a display) to provide notification information regarding the event based on the importance of the event.

Figure 6:
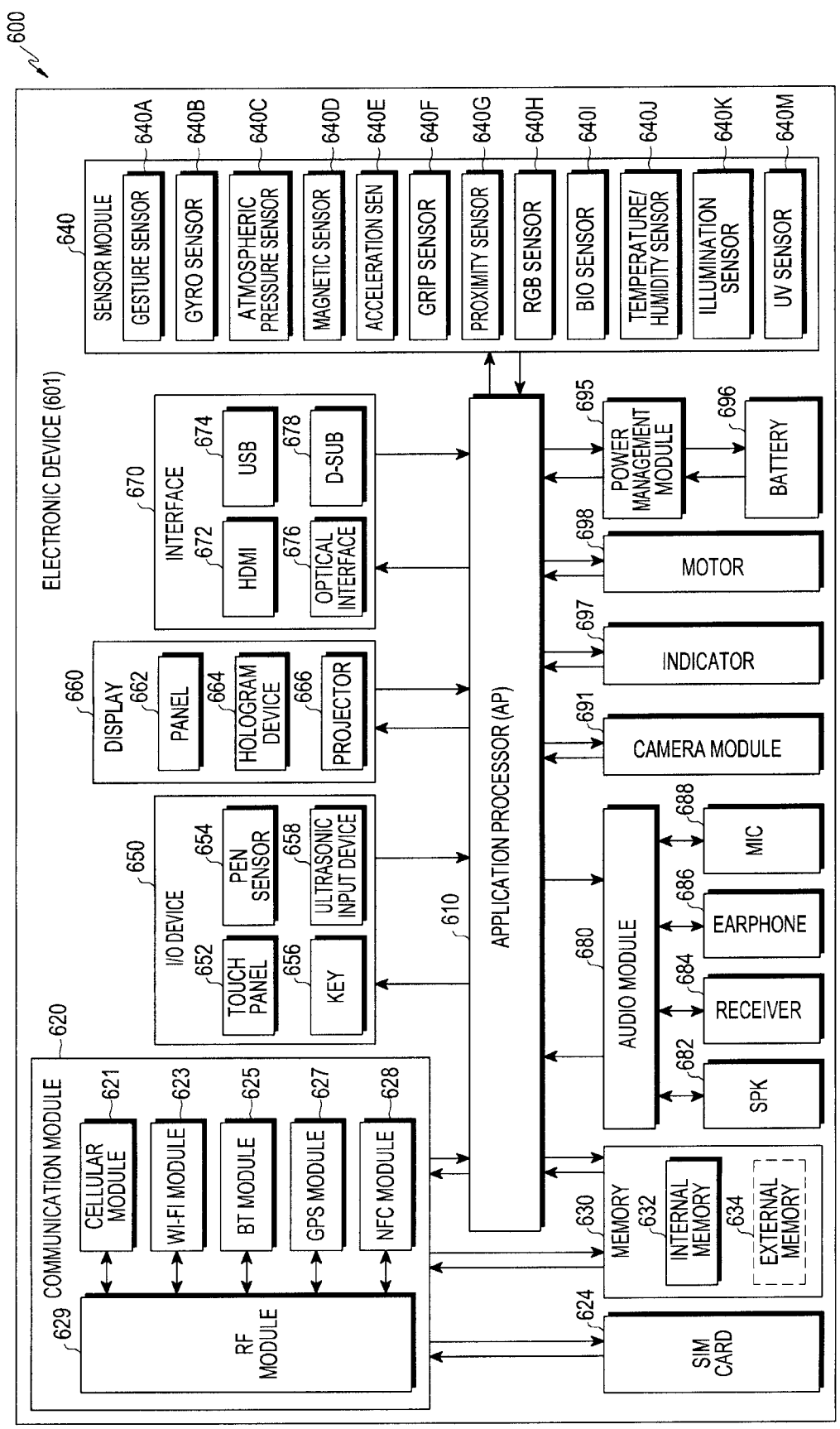
FIG. 6 is a block diagram of an example of an electronic device, according to aspects of the disclosure.

FIG. 6 is a block diagram of an example of an electronic device 601, according to another aspect of the present disclosure. The electronic device 601 may constitute the entire or some of the electronic device 101 shown in FIG. 1. Referring to FIG. 6, the electronic device 601 may include one or more Application Processors (APs) 610, a communication module 620, a Subscriber Identification Module (SIM) card 624, a memory 630, a sensor module 640, an input device 650, a display 660, an interface 670, an audio module 680, a camera module 691, a power manager module 695, a battery 696, an indicator 697, and a motor 698.

The AP 610 may control hardware and software components connected to the AP 610 by running an operating system or application programs, and perform data processing and operation. The AP 610 may include processor, such as an ARM-based processor, an x86 processor, a Field-Programmable Gate Array (FPGA), an Application-Specific Integrated Circuit, and/or any other suitable type of processor. For example, the AP 610 may be implemented by e.g., a System on Chip (SoC). In addition, the AP 610 may further include a Graphic Processing Unit (GPU).

The communication module 620 (corresponding to the communication interface 160 as shown in FIG. 1) may communicate data with other electronic devices, such as the external electronic device 104 and the server 106 connected via a network.

In accordance with aspects of the disclosure, the communication module 620 may include a cellular module 621, a Wi-Fi module 623, a BT module 625, a GPS module 627, an NFC module 628, and a Radio Frequency (RF) module 629.

The cellular module 621 may provide voice calls, video calls, SMS or Internet services over a communication network, such as LTE, LTE-A, CDMA, WCDMA, UMTS, WiBro, GSM, etc. The cellular module 621 may also identify and authenticate an electronic device in the communication network in cooperation with the SIM card 624. In accordance with aspects of the disclosure, the cellular module 621 may perform at least a part of functions that the AP 610 may provide. For example, the cellular module 621 may perform at least a part of multimedia control function.

In an aspect, the cellular module 621 may include a Communication Processor (CP). The cellular module 621 may also be implemented as part of a SoC, a standalone chip, and/or any other suitable type of electronic circuitry. While the components of FIG. 6, such as the cellular module 621 (e.g., a CP), the memory 630 or the power manager module 695 are illustrated as being separate from the AP 610, the AP 610 may incorporate some of the aforementioned components (e.g., the cellular module 621) in other aspects.

In accordance with aspects of the disclosure, the AP 610 or the cellular module 621 (e.g., a CP) may load a command or data received from at least one of a non-volatile memory or other components connected to the AP 610 or the cellular module 621, and then process the command or data. In addition, the AP 610 or the cellular module 621 may store data received from at least one of the other components or generated by at least one of the other components in a non-volatile memory.

The Wi-Fi module 623, the BT module 625, the GPS module 627, and the NFC module 628 may each include a processor for processing data sent or received through the corresponding module. While FIG. 6 illustrates each of the cellular module 621, the Wi-Fi module 623, the BT module 625, the GPS module 627, and the NFC module 628 as a separate block, some of them (e.g., two or more of them) may be incorporated in a single Integrated Chip (IC) or an IC package in other aspects. For example, at least some of processors corresponding to the cellular module 621, the Wi-Fi module 623, the BT module 625, the GPS module 627, and the NFC module 628, e.g., a CP of the cellular module 621 and a Wi-Fi processor of the Wi-Fi module 623 may be implemented in a single SoC.

The RF module 629 may perform data communication, more specifically, RF signal communication. The RF module 629 may include e.g., a transceiver, a Power Amp Module (PAM), a frequency filter, or a Low Noise Amplifier (LAN) (not shown). The RF module 629 may further include some parts for wireless communication, i.e., for transmitting or receiving RF signals over the air, such as conductors, wires, etc. While FIG. 6 illustrates that the cellular module 621, the Wi-Fi module 623, the BT module 625, the GPS module 627, and the NFC module 628 share the single RF module 629, at least one of them may perform RF signal communication through a separate RF module.

The SIM card 624 may include a subscriber identification module, and may be inserted into a slot formed in a particular position in the electronic device. The SIM card 624 may include a unique identification information, such as Integrated Circuit Card Identifier (ICCID), or subscriber information, such as International Mobile Subscriber Identity (IMSI).

The memory 630 (corresponding to the memory 130 of FIG. 1) may include an internal memory 632 or an external memory 634. The internal memory 632 may include e.g., at least one of a volatile memory, such as Dynamic Random Access Memory (DRAM), Static RAM (SRAM), Synchronous Dynamic RAM (SDRAM), or the like, or a non-volatile memory, such as One Time Programmable Read Only Memory (OTPROM), Programmable ROM (PROM), Erasable and Programmable ROM (EPROM), Electrically Erasable and Programmable ROM (EEPROM), mask ROM, flash ROM, NAND flash memory, Nor flash memory, or the like.

In an aspect, the internal memory 632 may be a Solid State Drive (SSD). The external memory 634 may include a flash drive, such as compact flash (CF), secure digital (SD), micro secure digital (Micro-SD), mini secure digital (Mini-SD), extreme digital (xD), memory stick, or the like. The external memory 634 may be operationally connected to the electronic device 601 through various interfaces. In an aspect, the electronic device 601 may further include a storage device (or a storage medium), such as a hard drive.

The sensor module 640 may measure a physical quantity or convert information measured or detected by monitoring the electronic device 601 to an electric signal. The sensor module 640 may include at least one of a gesture sensor 640A, a gyro sensor 640B, an atmospheric pressure sensor 640C, a magnetic sensor 640D, an acceleration sensor 640E, a grip sensor 640F, a proximity sensor 640G, a color sensor 640H such as an RGB (Red, Green, Blue) sensor, a bio sensor 640I, a temperature/humidity sensor 640J, an illumination sensor 640K, or an Ultra Violet (UV) sensor 640M.

Additionally or alternatively, the sensor module 640 may include an E-nose sensor, an electromyography (EMG) sensor, an electroencephalogram (EEG) sensor, an electrocardiogram (ECG) sensor, an infrared (IR) sensor, an iris sensor, a fingerprint sensor, or the like. The sensor module 640 may further include a control circuit for controlling at least one or more of the sensors included in the sensor module 640.

The input device 650 may include a touch panel 652, a (digital) pen sensor 654, a key 656, or an ultrasonic input device 658. The touch panel 652 may recognize touch inputs in at least one of capacitive, resistive, infrared, or ultrasonic methods. The touch panel 652 may further include a control circuit. With the resistive method, physical contact or proximity detection may be possible. The touch panel 652 may further include a tactile layer. In this regard, the touch panel 652 may provide the user with a tactile response.

The (digital) pen sensor 654 may be implemented in a way identical or similar to e.g., how a touch input of a user is received, or by using a separate sheet for recognition. The key 656 may include e.g., a physical button, optical key or key pad. The ultrasonic input device 658 may use an input tool that generates an ultrasonic signal and enable the electronic device 601 to determine data by sensing the ultrasonic signal to the microphone 688, thereby enabling wireless recognition. In an aspect, the electronic device 601 may receive a user input from an external device, such as a computer or a server through the communication module 620.

The display 660 (corresponding to the display 150 of FIG. 1) may include a panel 662, a hologram device 664, or a projector 666. The panel 662 may be, e.g., a Liquid Crystal Display (LCD), Active Matrix Organic Light Emitting Diodes (AMOLEDs), or the like. The panel 662 may be implemented to be flexible, transparent, or wearable. The panel 662 may also be incorporated with the touch panel 652 in a unit. The hologram device 664 may make three dimensional (3D) images (holograms) in the air by using light interference. The projector 666 may display an image by projecting light onto a screen. The screen may be, for example, located inside or outside of the electronic device 601. In accordance with aspects of the disclosure, the display 660 may further include a control circuit to control the panel 662, the hologram device 664, or the projector 666.

The interface 670 may include e.g., a High Definition Multimedia Interface (HDMI) 672, a USB 674, an optical interface 676, or a D-subminiature (D-sub) 678. The interface 670 may be included in e.g., the communication interface 160 shown in FIG. 1. Additionally or alternatively, the interface 670 may include a Mobile High-definition Link (MI-IL) interface, a secure digital (SD) card/multimedia card (MMC) interface, or IrDA standard interface.

The audio module 680 may convert a sound to an electric signal or vice versa. At least a part of the audio module 680 may be included in e.g., the I/O interface 140 as shown in FIG. 1. The audio module 680 may process sound information input or output through e.g., a speaker 682, a receiver 684, an earphone 686, or a microphone 688.

The camera module 691 may be a device for capturing still images and videos, and may include, in an aspect, one or more image sensors (e.g., front and back sensors), a lens, an Image Signal Processor (ISP), or a flash such as an LED or xenon lamp.

The power manager module 695 may manage power of the electronic device 601. Although not shown, e.g., a Power management Integrated Circuit (PMIC), a charger IC, or a battery or fuel gauge is included in the power manager module 695.

The PMIC may be mounted on e.g., an IC or an SOC. A charging method may be divided into wired and wireless charging methods. The charger IC may charge a battery and prevent overvoltage or overcurrent from being induced from a charger. In an aspect, the charger IC may be used in at least one of a cable charging scheme and a wireless charging scheme. The wireless charging scheme may include e.g., a magnetic resonance scheme, a magnetic induction scheme, or an electromagnetic wave based scheme, and an additional circuit, such as a coil loop, a resonance circuit, a rectifier, or the like may be added for wireless charging.

The battery gauge may measure an amount of remaining power of the battery 696, a voltage, a current, or a temperature while the battery 696 is being charged. The battery 696 may save or generate electricity, and supply power to the electronic device with the saved or generated electricity. The battery 696 may include, e.g., a rechargeable battery or a solar battery.

The indicator 697 may indicate a particular state of the electronic device 601 or a part of the electronic device (e.g., the AP 610), the particular state including e.g., a booting state, a message state, or charging state. The motor 698 may convert electric signals to mechanical vibration. Although not shown, a processing unit for supporting mobile TV, such as a GPU may be included in the electronic device 601. The processing unit for supporting mobile TV may process media data conforming to a standard for Digital Multimedia Broadcasting (DMB), Digital Video Broadcasting (DVB), or media flow.

Each of the aforementioned components of the electronic device may include one or more parts, and a name of the part may vary with a type of the electronic device. The electronic device in accordance with various aspects of the present disclosure may include at least one of the aforementioned components, omit some of them, or include other additional component(s). Some of the components may be combined into an entity, but the entity may perform the same functions as the components may do.

Figure 7:
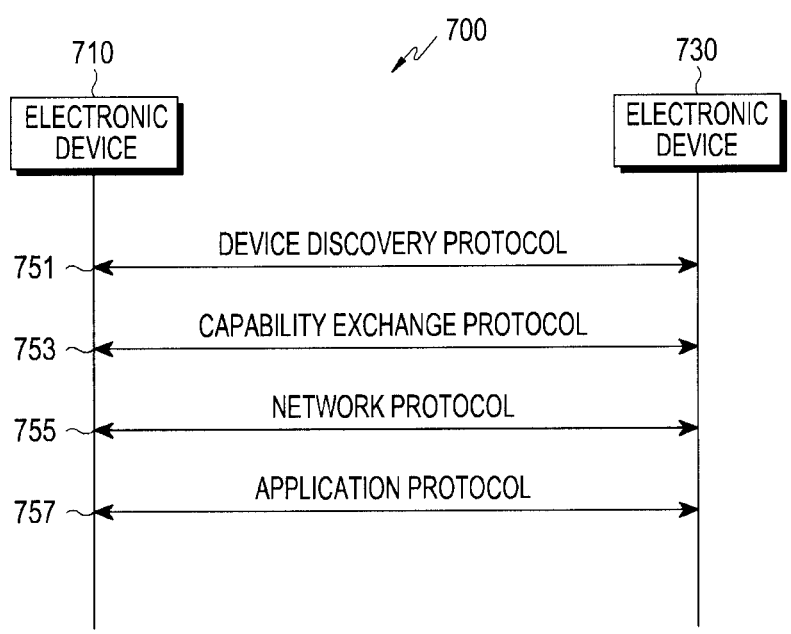
FIG. 7 is a diagram of an example of a communication protocol executed by a plurality of electronic devices, according to aspects of the disclosure.

FIG. 7 illustrates an example of a communication protocol 700 between multiple electronic devices 710 and 730, according to various aspects of the present disclosure. Referring to FIG. 7, the communication protocol 700 may include a device discovery protocol 751, a capability exchange protocol 753, a network protocol 755, and an application protocol 757.

In accordance with aspects of the disclosure, the device discovery protocol 751 may enable each of the electronic devices 710 and 730 to discover an external device that may be able to communicate with the electronic device 710 or 730 and to connect to the discovered device. For example, with the device discovery protocol 751, the electronic device 710 (corresponding to the electronic device 101) may detect the electronic device 730 (corresponding to the external electronic device 104 that may be able to communicate with the electronic device 710 by means of a communication scheme, such as W-Fi or USB that may be employed by the electronic device 710. With the device discovery protocol 751, the electronic device 710 may obtain and store information about identification of the discovered electronic device 730 in order to establish communication with the electronic device 730. The electronic device 710 may establish communication with the electronic device 730 based on the identification information.

In some aspects, the device discovery protocol 751 may be a protocol for mutual authentication among multiple electronic devices. For example, the electronic device 710 may perform an authentication procedure with the electronic device 730 based on communication information for access to at least one external electronic device, such as Media Access Control (MAC) address, Universally Unique Identifier (UUID), Subsystem Identification (SSID), Internet Protocol (IP) address, or the like.

In accordance with aspects of the disclosure, the capability exchange protocol 753 may be defined to exchange information associated with a service capability that may be supported by at least one of the electronic devices 710 an 730. For example, with the capability exchange protocol 753, the electronic devices 710 and 730 may exchange information associated with service capabilities being currently provided by them. The exchangeable information may include identification information indicating a particular service among a multiple services that may be supported by the electronic devices 710 and 730. For example, with the capability exchange protocol 753, the electronic device 710 may receive from the electronic device 730 identification information of a particular service provided by the electronic device 730. In this regard, the electronic device 710 may determine whether the electronic device 710 may support a particular service based on the received identification information.

In accordance with aspects of the disclosure, the network protocol 755 may be defined to control data flow between electronic devices 710 and 730 connected for communication, in order for the electronic devices 710 and 730 to provide a service in cooperation with each other. For example, at least one of the electronic devices 710 and 730 may perform error control, data quality control or the like, using the network protocol 755. Additionally or alternatively, the network protocol 755 may define a transfer format of data exchanged between the electronic devices 710 and 730. Furthermore, with the network protocol 755, at least one of the electronic devices 710 and 730 may manage at least a session (e.g., connect the session or terminate the session) for data exchange.

In accordance with aspects of the disclosure, the application protocol 757 may be defined to provide a procedure or information for exchanging data associated with a service to be provided to a foreign electronic device. For example, with the application protocol 757, the electronic device 710 may provide a service to the electronic device 730.

In accordance with aspects of the disclosure, the communication protocol 700 may include a standard communication protocol, a proprietary communication protocol defined by an individual or association (e.g., by a communication equipment manufacturer or a network provider), or a combination thereof.

The term 'module' may refer to a unit including one of hardware, software, and firmware, or a combination thereof. The term 'module' may be interchangeably used with a unit, logic, logical block, component, or circuit. The module may be a minimum unit or part of an integrated component. The module may be a minimum unit or part of performing one or more functions. The module may be mechanically or electrically implemented. For example, the module may include at least one of Application Specific Integrated Circuit (ASIC) chips, Field Programmable Gate Arrays (FPGAs), or Programmable Logic Arrays (PLAs) that perform some operations, which have already been known or will be developed in the future.

At least a part of the device (e.g., modules or their functions) or method (e.g., operations) may be implemented as instructions stored in a computer-readable storage medium e.g., in the form of a programming module. The instructions, when executed by one or more processor (e.g., the processor 122), may cause the processor to carry out a corresponding function. The computer-readable storage medium may be e.g., the memory 130. At least a part of the programming module may be implemented by e.g., the processor 210. At least a part of the programming module may include e.g., a module, program, routine, set of instructions, process, or the like for performing one or more functions.

Modules or programming modules in accordance with various aspects of the present disclosure may include at least one or more of the aforementioned components, omit some of them, or further include other additional components. Operations performed by modules, programming modules or other components in accordance with various aspects of the present invention may be carried out sequentially, simultaneously, repeatedly, or heuristically. Furthermore, some of the operations may be performed in a different order, or omitted, or include other additional operation(s). Furthermore, the operations disclosed in the flowcharts of FIGS. 3-5 are provided as examples only. At least some of these operations may be performed in a different order, performed concurrently, or altogether omitted.

In accordance with various aspects, provided is a storage medium having instructions stored thereon, the instructions, when executed by at least one processor, causing the at least one processor to perform at least one operation including: receiving a biological signal (e.g., a pulse signal) of a user in an electronic device, determining whether the electronic device is attached to or detached from the user based on at least the biological signal, and independently controlling a plurality of I/O devices (e.g., a display, a speaker, and a microphone) operationally connected to the electronic device (e.g., independently controlling the display, the speaker, and the microphone to be turned on or off), based on whether the electronic device is attached or detached from the user.

According to the various aspects of the present disclosure, an electronic device and method for controlling I/O devices may be able to selectively turn on or off a plurality of I/O devices, thereby preventing all of the plurality of I/O devices from being unnecessarily powered up, leading to reduction in current consumption of the electronic device.

Furthermore, the electronic device and method for controlling I/O devices may be able to control various I/O devices independently without any additional user input, thus giving the user increased convenience in using the I/O devices.

The above-described aspects of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

Unless otherwise stated, the examples presented herein are not mutually exclusive, but may be implemented in various combinations to achieve unique advantages. As these and other variations and combinations of the features discussed above can be utilized without departing from the disclosed subject matter as defined by the claims, the foregoing description of the embodiments should be taken by way of illustration rather than by way of limitation of the invention as defined by the claims. It will also be understood that the provision of examples aspects) of the invention (as well as clauses phrased as "such as," "including," "may," "for example," and the like) should not be interpreted as limiting the invention to the specific examples; rather, the examples are intended to illustrate only one of many possible embodiments.

It should be understood by those skilled in the art that many variations and modifications of the method and apparatus described herein will still fall within the spirit and scope of the present disclosure as defined in the appended claims and their equivalents.

What is claimed is:

1. A wearable electronic device comprising:
    a plurality of sensors including a first sensor and a second sensor;
    a communication module including circuitry;
    a haptic device;
    a memory configured to store instructions;
    a receiver module comprising circuitry configured to receive signals from the plurality of sensors including the first sensor and the second sensor; and
    at least one processor configured to execute the stored instructions to:
    receive, via the receiver module, a biological signal of a user from the first sensor and a movement signal of the wearable electronic device from the second sensor;
    determine if the wearable electronic device is worn based on the received biological signal; and
    determine if the wearable electronic device is moving based on the movement signal;
    receive, via the communication module, information corresponding to a communication event;
    process the communication event to provide a notification, such that the haptic device generates a vibrational movement if it is determined that the wearable electronic device is worn and that the wearable electronic device is moving; and
    process the communication event such that the haptic device does not generate the vibrational movement if it is determined that the wearable electronic device is not worn and that the wearable electronic device is not moving.

2. The wearable electronic device of claim 1, wherein the first sensor is configured to detect at least a heart rate of the user.

3. The wearable electronic device of claim 1, wherein the second sensor includes at least one of an acceleration sensor providing the movement signal.

4. The wearable electronic device of claim 1, wherein the communication event includes reception of a message by an external device to which the wearable electronic device is paired via the communication module, wherein an information corresponding to the reception of the message is received using a notification relay application stored in memory of the wearable electronic device.

5. The wearable electronic device of claim 4, further including a display,
    wherein the instructions are further executable by the at least one processor to:
    control the display to display a message notification when the haptic device is activated to generate the vibration movement.

6. The wearable electronic device of claim 1, wherein:
    the haptic device is activated when determining that the wearable electronic device is worn and a motion of the wearable electronic device is greater than a predetermined movement threshold, and
    power to the haptic device is reduced when determining that the wearable electronic device is worn and the motion of the wearable electronic device is less than the predetermined movement threshold.

7. A method in a wearable electronic device, comprising:
    receiving, by a receiver module including circuitry, a biological signal of a user as detected by a first sensor of the wearable electronic device;
    receiving, by the receiver module, a movement signal indicating whether the wearable electronic device is moving, as detected by a second sensor of the wearable electronic device;
    receiving, via a communication module of the wearable electronic device, information corresponding to a communication event;
    processing by at least one processor distinct from the receiver module the communication event to provide a notification, such that a haptic device of the wearable electronic device generates a vibrational movement if it is determined that the wearable electronic device is worn and moving; and
    processing by the at least one processor the communication event such that the haptic device does not generate the vibrational movement if it is determined that the wearable electronic device is not worn and that the wearable electronic device is not moving.

8. The method of claim 7, wherein the first sensor is configured to detect at least a heart rate of the user.

9. The method of claim 7, wherein the second sensor includes at least one of an acceleration sensor providing the movement signal.

10. The method of claim 7, wherein the communication event includes reception of a message by an external device to which the wearable electronic device is paired via the communication module, wherein an information corresponding to the reception of the message is received using a notification relay application stored in memory of the wearable electronic device.

11. The method of claim 10, further comprising: control a display of the wearable electronic device to display a message notification when the haptic device is activated to generate the vibration movement.

12. The method of claim 7, wherein:
the haptic device is activated when determining that the wearable electronic device is worn and a motion of the wearable electronic device is greater than a predetermined movement threshold, and
power to the haptic device is reduced when determining that the wearable electronic device is worn and the motion of the wearable electronic device is less than the predetermined movement threshold.

13. A non-transitory computer readable medium storing instructions executable by at least one processor to cause a wearable electronic device to:
receive, by a receiver module including circuitry, a biological signal of a user as detected by a first sensor of the wearable electronic device;
receive, by the receiver module, a movement signal indicating whether the wearable electronic device is moving as detected by a second sensor of the wearable electronic device;
receive, via a communication module of the wearable electronic device, information corresponding to a communication event;
process by at least one processor distinct from the receiver module the communication event to provide a notification, such that a haptic device of the wearable electronic device generates a vibrational movement if it is determined that the wearable electronic device is worn and moving; and
process by the at least one processor the communication event such that the haptic device does not generate the vibrational movement if it is determined that the wearable electronic device is not worn and that the wearable electronic device is not moving.

14. The non-transitory computer readable medium of claim 13, wherein the first sensor is configured to detect at least a heart rate of the user.

15. The non-transitory computer readable medium of claim 13, wherein the second sensor includes at least one of an acceleration sensor providing the movement signal.

16. The non-transitory computer readable medium of claim 13, wherein the communication event includes reception of a message by an external device to which the wearable electronic device is paired via the communication module, wherein an information corresponding to the reception of the message is received using a notification relay application stored in memory of the wearable electronic device.

17. The non-transitory computer readable medium of claim 16, further comprising: control a display of the wearable electronic device to display a message notification when the haptic device is activated to generate the vibration movement.

18. The non-transitory computer readable medium of claim 13, wherein:
the haptic device is activated when determining that the wearable electronic device is worn and a motion of the wearable electronic device is greater than a predetermined movement threshold, and
power to the haptic device is reduced when determining that the wearable electronic device is worn and the motion of the wearable electronic device is less than the predetermined movement threshold.

19. A wearable electronic device comprising:
a plurality of sensors including a first sensor and a second sensor;
a communication module including circuitry;
a haptic device;
a memory configured to store instructions; and
at least one processor configured to execute the stored instructions to:
receive a biological signal of a user from the first sensor and a movement signal of the wearable electronic device from the second sensor;
determine if the wearable electronic device is worn based on the received biological signal;
identify one of plurality of states of a user based on the received movement signal of the wearable electronic device;
receive, via the communication module, information corresponding to a message reception event;
process the information corresponding to the message reception event to provide a notification;
in response to the information corresponding to the message reception event, control the haptic device to generate a vibrational movement if it is determined that the wearable electronic device is worn and that the identified state is a first state; and
in response to the information corresponding to the message reception event, control the haptic device not to generate a vibrational movement if it is determined that the wearable electronic device is worn and that the identified state is a second state.

20. The wearable electronic device of claim 19, wherein the first sensor is configured to detect at least a heart rate of the user.

21. The wearable electronic device of claim 19, wherein the second sensor includes at least one of an acceleration sensor providing at least a part of the movement signal.

22. The wearable electronic device of claim 19, wherein the information corresponding to the message reception event is received using a notification relay application stored in memory of the wearable electronic device from an external device to which the wearable electronic device is paired via the communication module.

23. The wearable electronic device of claim 19, further comprising a receiver module comprising circuitry configured to receive signals from the plurality of sensors including the first sensor and the second sensor.

* * * * *